United States Patent
Nakagawa

(10) Patent No.: US 7,565,826 B2
(45) Date of Patent: Jul. 28, 2009

(54) GAS SENSOR

(75) Inventor: Kazuya Nakagawa, Kariya (JP)

(73) Assignee: Denso Corporation, Kariya (JP)

( * ) Notice: Subject to any disclaimer, the term of this patent is extended or adjusted under 35 U.S.C. 154(b) by 410 days.

(21) Appl. No.: 11/651,071

(22) Filed: Jan. 9, 2007

(65) Prior Publication Data

US 2007/0157939 A1 Jul. 12, 2007

(30) Foreign Application Priority Data

Jan. 12, 2006 (JP) .............................. 2006-005124
Oct. 6, 2006 (JP) .............................. 2006-275341

(51) Int. Cl.
*G01N 7/00* (2006.01)
(52) U.S. Cl. ...................................... 73/23.2
(58) Field of Classification Search ................... 73/23.2
See application file for complete search history.

(56) References Cited

U.S. PATENT DOCUMENTS

| 6,546,783 B2 * | 4/2003 | Shirai ......................... 73/31.05 |
| 6,637,256 B2 * | 10/2003 | Shirai ......................... 73/31.05 |
| 6,813,930 B2 * | 11/2004 | Kimata et al. .............. 73/31.05 |
| 7,159,447 B2 * | 1/2007 | Nakagawa ................. 73/31.05 |
| 7,178,382 B2 * | 2/2007 | Noda et al. ................. 73/31.05 |
| 2002/0000116 A1 * | 1/2002 | Kimata et al. .............. 73/31.05 |
| 2002/0017128 A1 * | 2/2002 | Shirai ......................... 73/31.05 |
| 2005/0178187 A1 * | 8/2005 | Nakagawa ................. 73/31.05 |
| 2006/0117832 A1 * | 6/2006 | Nakashima et al. .......... 73/23.2 |

FOREIGN PATENT DOCUMENTS

| JP | 2001-235445 | 8/2001 |
| JP | 2002-131270 A | 5/2002 |
| JP | 2002-286685 A | 10/2002 |

* cited by examiner

*Primary Examiner*—Hezron Williams
*Assistant Examiner*—Rodney T Frank
(74) *Attorney, Agent, or Firm*—Nixon & Vanderhye, PC

(57) ABSTRACT

A gas sensor is disclosed as having a gas sensor element, supported with a cylindrical housing, which is covered with an atmosphere-side cover fixedly secured to the cylindrical housing. The atmosphere-side cover fixedly supports a seal member having a ventilation bore and a plurality of lead wire inserting bores formed around the ventilation bore. A filter member is fusion bonded to the seal member in a fusion-bonded area at temperatures above 300° C. The fusion-bonded area is formed in an entire circumference in gastight effect at an area outside an outer periphery of the ventilation bore and has no clearance, wherein suppose that the ventilation bore has an opening surface area A at the end face of the seal member and a region surrounded with the fusion-bonded area has a surface area B, the relationship is established as $A<B \leqq 9A$.

10 Claims, 5 Drawing Sheets

GAS SENSOR

CROSS REFERENCE TO RELATED APPLICATIONS

This application is based on Japanese Patent Application Nos. 2006-5124, filed on Jan. 12, 2006, and 2006-275341, filed on Oct. 6, 2006, the contents of which are hereby incorporated by reference.

BACKGROUND OF THE INVENTION

1. Technical Field of the Invention

The present invention relates to a gas sensor mounted on an exhaust gas pipe of an automotive engine for detecting a concentration of specified gas in measuring gases passing through the exhaust gas pipe.

2. Description of the Related Art

In related art, various attempts have heretofore been to provide gas sensors adapted to be mounted on exhaust systems of internal combustion engines such as engines of motor vehicles for measuring a concentration of specified gas such as oxygen gas contained in exhaust gases to allow a detected output to be sued for controlling an air fuel ratio. Such gas sensors include a gas sensor of an atmospheric air introduction type as disclosed in Japanese Unexamined Patent Application Publication No. 2002-131270.

Under a circumstance where the gas sensor of such a type is mounted on the exhaust pipe of the automotive engine, a distal end of the gas sensor is exposed to measuring gases with a base end of the gas sensor being exposed to atmospheric environment. In addition, the gas sensor includes a cylindrical case, fixedly secured to a base end portion of the gas sensor so as to cover a base end of a gas sensor element for detecting a gas concentration, a seal member closing an open end of the case, and a ventilation filter covering a ventilation bore through which atmospheric air is introduced. In order to provide an ease of assembling the seal member and the ventilation filter with respect to each other, the ventilation and the seal member are integrally assembled to each other by die forming.

With the gas sensor of such a related art structure, however, the seal member and the ventilation filter are bonded to each other through a mechanical connection such as mechanical clipping or caulking techniques. This results in a decrease of bonding strength of the ventilation filter and, hence, the ventilation filter has needed to be bonded in a widened joint area. This causes an edge portion of the ventilation filter to cover lead wire insertion bores formed in the seal member, causing an issue to arise in impeding the insertion of the lead wires into the seal member. This results in a difficulty in minimizing a whole of the seal member.

SUMMARY OF THE INVENTION

The present invention has been completed with a view to addressing the above issues and has an object to provide a gas sensor that is minimized in structure without causing a conflict between a ventilation filter and lead wire insertion bores formed in a seal member.

To achieve the above object, one aspect of the present invention provides a gas sensor comprising a gas sensor element for detecting a concentration of specified gas in measuring gases, a cylindrical housing through which the sensor element extends and is fixedly supported, and an atmosphere-side cover fixedly secured to a base end of the cylindrical housing so as to cover a base end portion of the gas sensor element. A seal member is fixedly supported with a base end of the atmosphere-side cover and having a ventilation bore, through which atmospheric air is introduced to the cylindrical housing, and a plurality of lead wire inserting bores formed around the ventilation bore. A filter member, made of porous material and covering the ventilation bore so as to permeate atmospheric air, has a fusion-bonded area in which the filter member is fusion bonded to an end face of the seal member at temperatures above 200° C. The fusion-bonded area is formed in an entire circumference in gastight effect at an area outside an outer periphery of the ventilation bore covered with the filter member and has no clearance. Suppose that the ventilation bore has an opening surface area A at the end face of the seal member and a region surrounded with the fusion-bonded area has a surface area B, the relationship is established as $A < B \leq 9A$ With the ventilation bore supposed to have the opening surface area A at the end face of the seal member and the region, surrounded with the fusion-bonded area, supposed to have the surface area B, the relationship is established as $A < B \leq 9A$. This prevents the ventilation filter from straddling over the lead wire insertion bores formed in the seal member. Further, the ventilation bore and the lead wire insertion bores can be made closer to each other in distance, enabling the seal member to be minimized in structure. Furthermore, the seal member and the filter member can be tightly bound due to fusion bonding. In addition, since the seal member and the filter member are fusion bonded to each other at temperatures above 200° C., the seal member and the filter member can sustain in a bonded state like a status even under circumstances where a gas sensor is used under high temperature environments above 200° C. Moreover, no clearance is created between the seal member and the filter member, no foreign substance is permitted to penetrate into an inside of the gas sensor.

With the gas sensor of the present embodiment, the ventilation bore may be formed in the seal member so as to extend in an axial direction, and the filter member covers an end of the ventilation bore at the end face of the seal member.

Such arrangement enables the filter member to be located at a position remote from a distal end of the gas sensor exposed to measuring gases prevailing at high temperatures. This prevents the pores of the filter member, made of porous material, from being affected to melt and deform due to high heat while clogging with the resultant deterioration in air permeability.

With the gas sensor of the present embodiment, the atmosphere-side cover may comprise a main cylindrical cover body having one end connected to the cylindrical housing, an annular shoulder extending radially inward from the other end of the main cylindrical cover body, and a secondary cylindrical cover body axially extending from the annular shoulder of the main cylindrical cover body and having the base end with which the seal member is fixedly supported, and further comprising an element-side insulator accommodated in the cylindrical housing and fixedly supporting the gas sensor element, and an atmosphere-side insulator disposed between the element-side insulator and the annular shoulder of the main cylindrical housing.

With such a structure of the gas sensor, since the atmosphere-side cover comprises the main cylindrical cover body and the secondary cylindrical cover body extending from the main cylindrical cover body via the annular shoulder thereof, the atmosphere-side cover can be simply manufactured with high precision on a mass production basis. In addition, the element-side insulator is accommodated in the cylindrical housing and fixedly supports the gas sensor element, the gas sensor element can be reliably supported in electrical insulation with the housing. This ensures reliable operation of the gas sensor element. Moreover, the atmosphere-side insulator is fixedly retained with the annular shoulder of the atmosphere-side cover to retain the element-side insulator in a fixed place. Thus, the gas sensor element is fixedly retained in the housing in a reliable manner using a simplified structure, enabling reduction in production cost while achieving reliable operation of the gas sensor element.

With the present embodiment, the gas sensor may further comprise a packing member disposed between the element-side insulator and the cylindrical housing to provide a gastight sealing effect therebetween, and a spring member disposed between the atmosphere-side insulator and the annular shoulder of the main cylindrical housing to press the element-side insulator and the atmosphere-side insulator against the packing member.

The presence of the packing member disposed between the element-side insulator and the cylindrical housing provide a reliable gas tight sealing effect therebetween. This prevents measuring gases from penetrating into a compartment where electrical component parts exist. Thus, no electrical part is exposed to harmful measuring gases, ensuring a long operating life of the gas sensor. In addition, since the spring member is disposed between the atmosphere-side insulator and the annular shoulder of the main cylindrical housing, the element-side insulator can be held in pressed contact with the packing member. This allows the element-side insulator to be supported with the housing in reliable gastight sealing effect, enabling the gas sensor to continuously operate for a long operating life.

With the gas sensor of the present embodiment, the atmosphere-side cover may comprise a main cylindrical cover body having one end connected to the cylindrical housing, an annular shoulder extending radially inward from the other end of the main cylindrical cover body, and a secondary cylindrical cover body axially extending from the annular shoulder of the main cylindrical cover body and having the base end with which the seal member is fixedly supported, and the cylindrical housing has a base end portion formed with an inner bore and having a distal end formed with an annular flange extending radially inward, and further comprising a cylindrical insulator accommodated in the inner bore of the cylindrical housing and an annular spring member disposed between the annular flange of the cylindrical housing and one end of the cylindrical insulator.

With such a structure of the gas sensor, since the atmosphere-side cover comprises the main cylindrical cover body and the secondary cylindrical cover body extending from the main cylindrical cover body via the annular shoulder thereof, the atmosphere-side cover can be simply manufactured with high precision on a mass production basis. In addition, the cylindrical insulator is accommodated in the cylindrical housing and fixedly supports the gas sensor element, the gas sensor element can be reliably supported in electrical insulation with the housing. This ensures reliable operation of the gas sensor element. Moreover, the cylindrical insulator is fixedly retained with the annular shoulder of the cylindrical housing to retain the cylindrical insulator in a fixed place. Thus, the gas sensor element is fixedly retained in the housing in a reliable manner using a simplified structure, enabling reduction in production cost while achieving reliable operation of the gas sensor element.

With the present embodiment, the gas sensor may further comprise further comprises a heater element disposed inside the gas sensor element, and an insulator guide fixedly supported with the atmosphere-side cover for accommodating connecting members through which electrode terminals of the gas sensor element and electrode terminals of the heater element are connected to lead wires, respectively.

With such a structure of the gas sensor, since the gas sensor element incorporates therein the heater element and the connecting members, through which electrode terminals of the gas sensor element and electrode terminals of the heater element are connected to lead wires, are guided with the insulator guide, the electrical component parts are held in electrical insulating effect in a reliable fashion. This ensures reliable operation of the gas sensor even under usage in a vehicle running on rough roads.

With the gas sensor of the present embodiment, the atmosphere-side cover may comprise a main cylindrical cover body having one end connected to the cylindrical housing, an annular shoulder extending radially inward from the other end of the main cylindrical cover body, and a secondary cylindrical cover body axially extending from the other end of the main cylindrical cover body and having a first portion, with which the seal member is fixedly supported, and a second portion axially spaced from the first portion in a position close to the main cylindrical cover body, and the cylindrical housing has a base end portion formed with an inner bore and having a distal end formed with an annular flange extending radially inward, and further comprising a cylindrical insulator accommodated in the inner bore of the cylindrical housing and an annular spring member disposed between the annular flange of the cylindrical housing and one end of the cylindrical insulator.

With such a structure of the gas sensor, since the atmosphere-side cover comprises the main cylindrical cover body and the secondary cylindrical cover body extending from the main cylindrical cover body, the atmosphere-side cover can be simply manufactured with high precision on a mass production basis. In addition, the cylindrical insulator is accommodated in the cylindrical housing and fixedly supports the gas sensor element, the gas sensor element can be reliably supported in electrical insulation with the housing. This ensures reliable operation of the gas sensor element. Moreover, the cylindrical insulator is fixedly retained with the annular shoulder of the cylindrical housing to retain the cylindrical insulator in a fixed place. Thus, the gas sensor element is fixedly retained in the housing in a reliable manner using a simplified structure, enabling reduction in production cost while achieving reliable operation of the gas sensor element.

With the present embodiment, the gas sensor may further comprise a heater element disposed inside the gas sensor element, and an insulator guide fixedly supported with the second portion of the secondary cylindrical cover body for accommodating connecting members through which electrode terminals of the gas sensor element and electrode terminals of the heater element are connected to lead wires, respectively.

With such a structure of the gas sensor, since the gas sensor element incorporates therein the heater element and the connecting members, through which electrode terminals of the gas sensor element and electrode terminals of the heater element are connected to lead wires, are guided with the insulator guide supported with the second portion of the atmosphere-side cover, the electrical component parts are held in electrical insulating effect in a reliable fashion. This ensures reliable operation of the gas sensor even under usage in a vehicle running on rough roads.

With the gas sensor of the present embodiment, the filer member may have an outer circumferential periphery located inside the plurality of lead wire insertion bores formed in the seal member.

Such an arrangement enables the filter member to be prevented from straddling over the lead wire insertion bores formed in the seal member, providing ease of assembling the ventilation film to the seal member. This enables a reduction in man hour to insert lead wires into the associated lead wire insertion bores, achieving a reduction in production cost.

With the gas sensor of the present embodiment, the filer member may have an outer circumferential periphery, extending in an area outside the plurality of lead wire insertion of the seal member, and has a plurality of bores formed at the same positions at which the plurality of lead wire insertion bores are formed in the seal member.

With such a configuration, since the filer member has a plurality of bores formed at the same positions as the lead wire insertion bores, the lead wires can be easily inserted to the lead wire insertion bores of the seal member, resulting in a reduction of production cost.

DETAILED DESCRIPTION OF PREFERRED EMBODIMENTS

Figure 1:
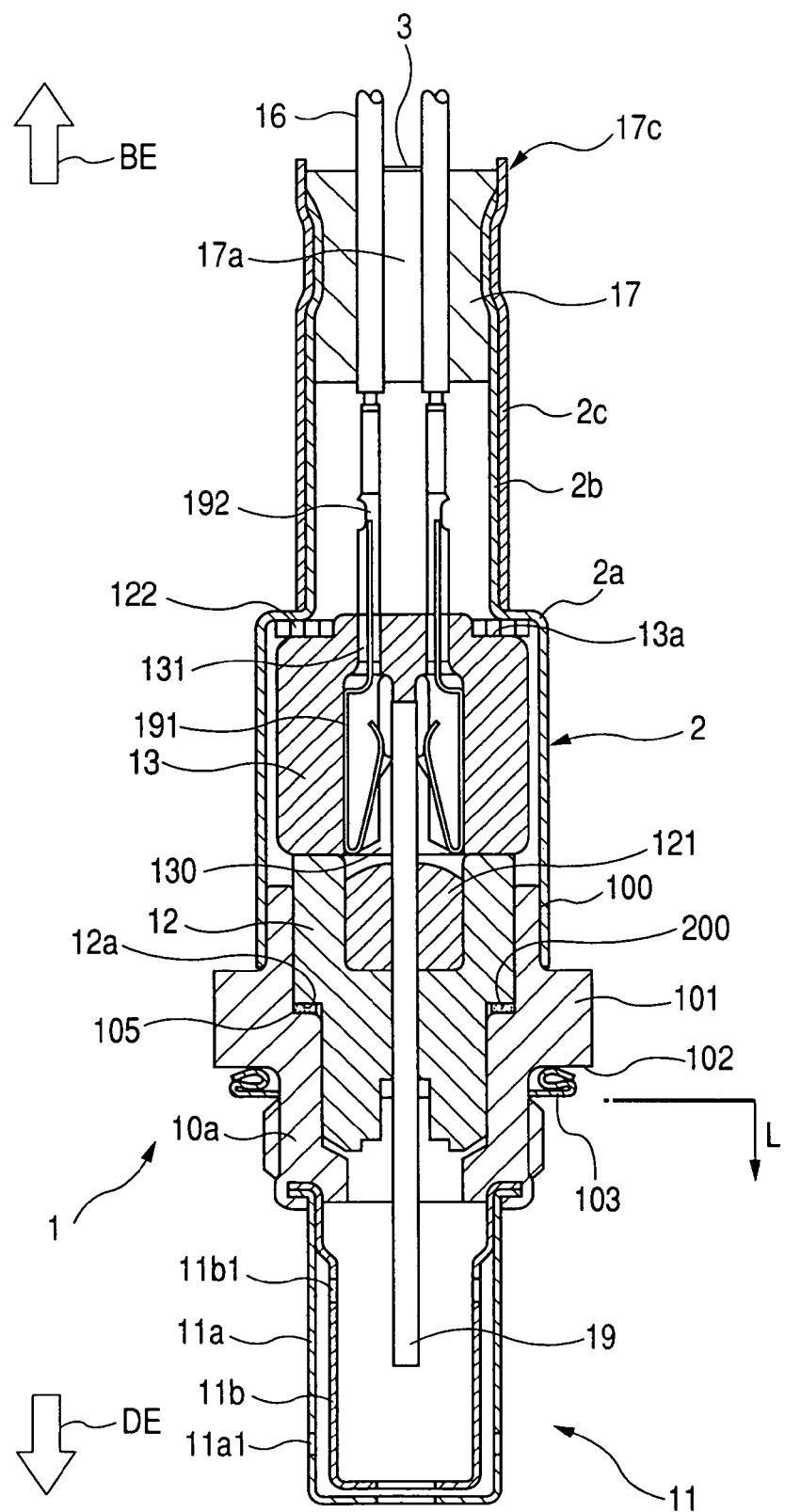
FIG. 1 is a longitudinal sectional view of a gas sensor of a first embodiment according to the present invention.

Now, gas sensors of various embodiments according to the present invention are described below in detail with reference to the accompanying drawings. However, the present invention is construed not to be limited to such embodiments described below and technical concepts of the present invention may be implemented in combination with other known technologies or the other technology having functions equivalent to such known technologies.

In the following description, like reference characters designate like or corresponding parts throughout the several views. Also, in the following description, it is construed that a portion of a gas sensor available to be inserted to an exhaust gas pipe of an internal combustion engine of a motor vehicle is referred to as a "distal end" oriented in a direction indicated by an arrow DE in FIG. 1 and an opposite side of the gas sensor exposed to an atmosphere is referred to as a "base end" or "base end portion" oriented in a direction indicated by an arrow BE in FIG. 1.

Also, it will be appreciated that the gas sensors of various embodiment according to the present invention may have a wide variety of applications to an oxygen sensor, an A/F sensor, a NOx sensor, etc.

First Embodiment

A gas sensor of a first embodiment according to the present invention is described below in detail with reference to FIG. 1 and FIGS. 2A to 2C.

Figure 2A:
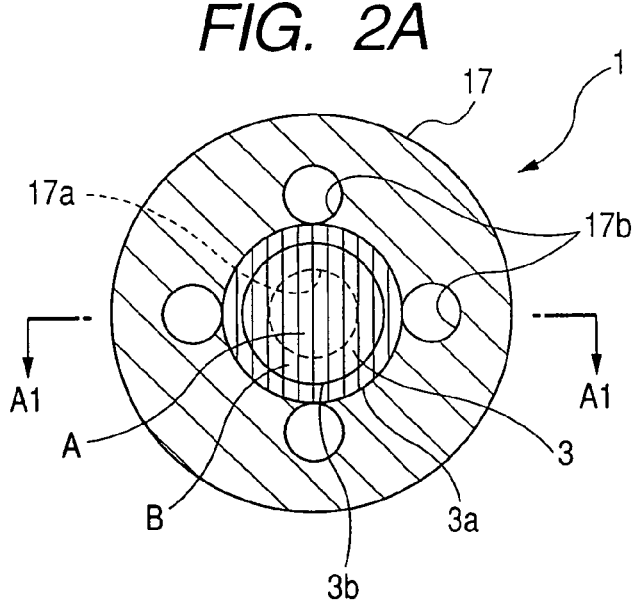
FIG. 2A is a cross sectional view showing the relationship between a seal member and a ventilation filter.
Figure 2B:
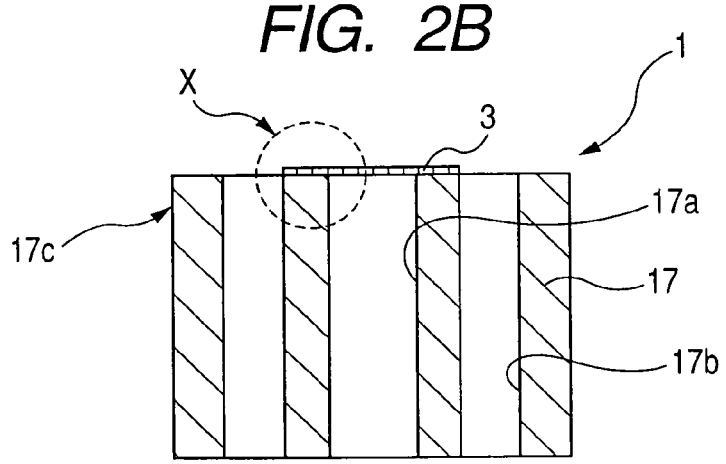
FIG. 2B is a cross sectional view taken on line along A1-A1 of FIG. 2A.
Figure 2C:
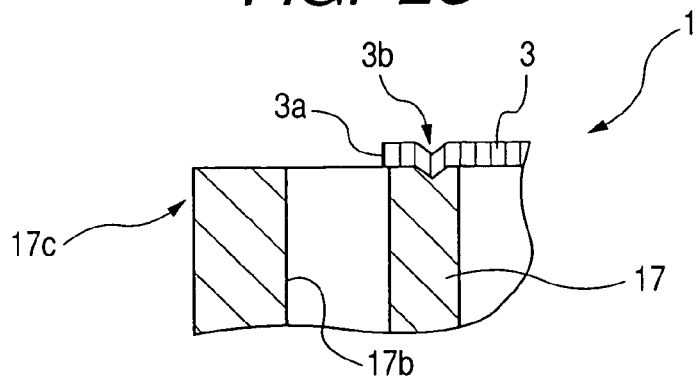
FIG. 2C is a fragmentary cross sectional view of the seal member and the ventilation filter in enlarged scales.

FIG. 1 is a longitudinal cross sectional view showing an overall structure of the gas sensor of the present embodiment. FIG. 2A is an enlarged view of showing a seal member 17 and a ventilation filter 3 shown in FIG. 1. FIG. 2B is a cross sectional view taken on line A1-A1 of FIG. 2A and FIG. 2C is an enlarged view showing a segmented area encircled by a circle line X in FIG. 2B.

As shown in FIG. 1 and FIGS. 2A to 2C, a gas sensor 1 of the present embodiment comprises a gas sensor element 19 operative to detect a specified gas concentration of measuring gases, a cylindrical housing 10 through which the gas sensor element 19 extends and is fixed supported, a cylindrical measuring gas-side cover 11 fixedly secured to a distal end of the housing 10 so as to cover a distal end of the gas sensor element 19, and a cylindrical atmosphere-side cover 2 fixedly secured to the housing 10 at a base end thereof so as to cover a base end of the gas sensor element.

Further, the atmosphere-side cover 2 has a base end into which a seal member 17 is accommodated in a fixed place. The seal member 17 has a central area formed with an axially extending ventilation bore 17a for introducing atmospheric air to an inside of the atmosphere-side cover 2. The seal member 17 also has a plurality of axially extending lead wire insertion bores 17b formed at circumferentially spaced positions in an area around the ventilation bore 17a.

With the gas sensor 1 of the present embodiment, a ventilation filter 3 is fusion bonded to a base end portion 17c of the seal member 17 in a fusion-bonded area 3b at temperatures above 300° C. (that is, at temperatures above melting point of the filter). The fusion-bonded area 3b can be formed upon causing an annular heating member with a diameter smaller than that of the ventilation filter 3 to rise at a temperature higher than 300° C. and pressing the annular heating member against the seal member 17 via the ventilation filter 3.

Further, locating the ventilation filter 3 at the base end portion 17c of the seal member 17 enables the ventilation filter 3 to be positioned remote from a distal end of the gas sensor 1. Such a placement provides capability of preventing pores of the ventilation filter 3, made of porous material, from being melted in deformation and stopped up due to heat with the resultant deterioration in air permeability.

Furthermore, the fusion-bonded area 3b, made of the seal member 17 and the ventilation filter 3 which are fusion-bonded to each other, is formed in an entire circumference with no clearance being formed at the fusion bonded portion. With such an arrangement, no clearance is formed between the seal member 17 and the ventilation filter 3, thereby preventing foreign substances from penetrating into the gas sensor 1 from an outside.

Moreover, suppose a surface area of the ventilation bore 17a of the base end portion 17c of the seal member 17 in a radial direction is "A" and a surface area of a region surrounded with the fusion-bonded area 3b is "B", then, the relationship is established as $$A < B \leq 9A$$

Thus, no annular edge portion 3a of the ventilation filter 3 flops over the lead wire insertion bores 17b formed in the seal member 17. In addition, such a structure enables the ventilation bore 17a and the lead wire insertion bores 17b to be placed closer in distance to each other, thereby making it possible to minimize a whole of the seal member 17.

Meanwhile, with the related art mechanical joining method such as a sandwiching method, with a view to obtaining reliable joining, the seal member 17 and the ventilation filter 3 need to be pressed against each other with a greater pressing force than that required for fusion-bonding. In such a case, a need arises for the joining portion to have an increased surface area for the purpose of precluding the deformation in shape of the ventilation bore 17a of the seal member 17 and preventing the ventilation filter 3 from dropping into the ventilation bore 17a upon receipt of such a pressing force. Thus, with the related art joining method, the surface area B of the joint portion has been greater than the surface area A of the ventilation bore. Although a difference appears depending on design content, with the surface area of the joint portion needed in the related art joining method, the surface area "B" of the joint portion with respect to the surface area "A" of the ventilation bore was established in the relationship expressed as $$B > 9A$$

As set forth above, with the gas sensor 1 of the present embodiment adopting the structure set forth above, no annular edge portion 3a of the ventilation filter 3 flops over the lead wire insertion bores 17b of the seal member 17.

In actual practice, the gas sensor 1 of the present embodiment is mounted on a wall surface of an exhaust pipe extending from an automotive engine and measures an air fuel ratio of the automotive engine to provide an air fuel ratio signal for use in controlling an air fuel ratio. The gas sensor 1 is mounted on the wall surface of the exhaust pipe so as to allow an end face 102 of a metallic housing body 101 radially protruding from a sidewall of the housing 10 to face an outer wall surface of the exhaust pipe. In addition, a gasket 103 is placed on the end face 102 of the metallic housing body 101 so as to allow the metallic housing body 101 to be fixedly secured onto the exhaust pipe of the automotive engine in a gastight relationship.

With the gas sensor 1 mounted on the exhaust pipe of the automotive engine, a region including a cylindrical extension 10a below a line L (see FIG. 1) and the measuring gas-side cover 11 constitutes an area exposed to high temperature exhaust gases flowing through the exhaust pipe during the operation to measure the air fuel ratio, while a base end portion above the line L is exposed to atmosphere. With such a configuration, the temperature of the gas sensor 1 gradually decreases along the base end of the gas sensor 1 to be remote from the line L. Also, an upper area of the gas sensor 1 is referred to as the base end side designated at BE and the lower area referred to as the distal end DE in FIG. 1.

The distal end of the housing 10 carries thereon the measuring gas-side cover 11 that takes the form of a structure including an outer cover 11a and an inner cover 11b. The outer cover 11a and the inner cover 11b are formed with gas flow passages 11a1, 111b1, respectively, which are placed at positions offset from each other in a radial direction of the gas sensor 1. In addition, the inner cover 11b accommodates therein the distal end of the gas sensor element 19.

The gas sensor element 19 is fixedly supported with the housing 10 by means of an element-side insulator 12. The element-side insulator 12 is fitted to an interior of the housing 10 and has an annular shoulder 12a resting on a tapered annular shoulder 105 of the housing 10. Metallic packing 200 is sandwiched between the annular shoulder 12a of the element-side insulator 12 and the annular shoulder 105 of the housing 10 to provide a gastight sealing effect for suppressing the flow of gas.

The element-side insulator 12 carries thereon an atmosphere-side insulator 13 having a base portion formed with an annular shoulder 13a. In addition, the atmosphere-side cover 2 has an end portion tightly fitted to a base end of the housing 10 and a base end portion formed with an annular flange 2a. A disc spring 122 is interposed between the annular shoulder 13a of the atmosphere-side insulator 13 and the annular shoulder 2a of the atmosphere-side cover 2 for applying a restoring force to an end face of the base end of the element-side insulator 12 along an axial direction (that is, in a direction parallel to a central axis of the gas sensor 1 formed in a substantially cylindrical shape) of the gas sensor 1. This restoring force of the disc spring 122 biases the annular shoulder 12a of the element-side insulator 12 against the tapered annular shoulder 105 of the housing 10.

The atmosphere-side insulator 13 is internally formed with a cavity portion 130 that accommodates therein a base end of the gas sensor element 19. The atmosphere-side insulator 13 has a base end formed with a through-bore 131 providing communication between the cavity portion 130 of the atmosphere-side insulator 13 and a space facing the end face of the atmosphere-side insulator 13.

Electrode terminals 191 are accommodated I the cavity portion 130 of the atmosphere-side insulator 13 and held in electrical contact with the base end of the gas sensor element 19 to extract a detected output of the gas sensor element 19 to the outside while supplying electric power thereto. The electrode terminals 191 extend through the through-bore 131 into a cylindrical space defined inside the atmosphere-side cover 2 in an area outside the atmosphere-side insulator 13. The electrode terminals 191 are electrically connected to the lead wires 16 through connecting members 192 in the cylindrical space.

The lead wires 16 are extracted to the outside of the gas sensor element 1 for connection to a measuring device, located outside of the gas sensor 1, and a power supply.

The atmosphere-side cover 2 comprises an inner cover 2b and an outer cover 2c. The inner cover 2b is made of stainless steel (SUS304) to have a substantially cylindrical shape and directly secured to an outer periphery 100 of the base end of the housing 10 by welding. The outer cover 2c is made of stainless steel (SUS304) to have a substantially cylindrical shape and covers a circumferential periphery of a base end of the inner cover 2b, with the inner cover 2b and the outer cover 2c being caulked from an outside area.

The seal member 17 is made of fluorocarbon rubber to have a column-shape and has the central area formed with the ventilation bore 17a around which the plurality of the lead wire insertion bores 17b.

The ventilation filter 3 is made of material, having a porous structure and high air permeability, which includes polytetrafluoroethylene (PTFE).

Meanwhile, with the gas sensor 1 of the present embodiment, the ventilation filter 3 is fusion bonded to the base end portion 17c of the seal member 17 in the fusion-bonded area 3b at temperatures above 300° C. The fusion-bonded area 3b can be formed upon causing the annular heating member with the diameter smaller than that of the ventilation filter 3 to rise at the temperature higher than 300° C. and pressing the annular heating member against the seal member 17 via the ventilation filter 3.

Further, the fusion-bonded area 3b, resulting from fusion bonding locating the seal member 17 and the ventilation filter 3, is formed in an entire circumference with no clearance being provided in the bonding area. With such an arrangement, no clearance is formed between the seal member 17 and the ventilation filter 3, and no foreign substances penetrate into the gas sensor 1 from the outside.

Furthermore, locating the ventilation filter 3 at the base end portion 17c of the seal member 17 enables the ventilation filter 3 to be positioned remote from a distal end of the gas sensor 1 exposed to measuring gases prevailing at high temperatures. Such a placement provides capability of preventing pores of the ventilation filter 3, made of porous material, from being melted in deformation and stopped up due to heat with the resultant deterioration in air permeability.

Furthermore, the surface area A of the ventilation bore 17a in the radial cross section of the base end portion 17c of the seal member 17 lies in a value of 1 mm² and the surface area B of the region surrounded with the fusion-bonded area 3b lies in a value of 9 mm², and the relationship is established as $A < B \leq 9A$ Thus, no annular edge portion 3a of the ventilation filter 3 flops over the lead wire insertion bores 17b formed in the seal member 17. In addition, such a structure enables the ventilation bore 17a and the lead wire insertion bores 17b to be placed closer in distance to each other, thereby making it possible to minimize a whole of the seal member 17.

As set forth above, with the gas sensor 1 adopting such a structure, the gas sensor can be miniaturized in structure without causing the annular edge portion 3a of the ventilation filter 3 from flopping over the lead wire insertion bores 17b formed in the seal member 17.

Second Embodiment

A gas sensor of a second embodiment according to the present invention is described below with reference to FIG. 3.

Figure 3:
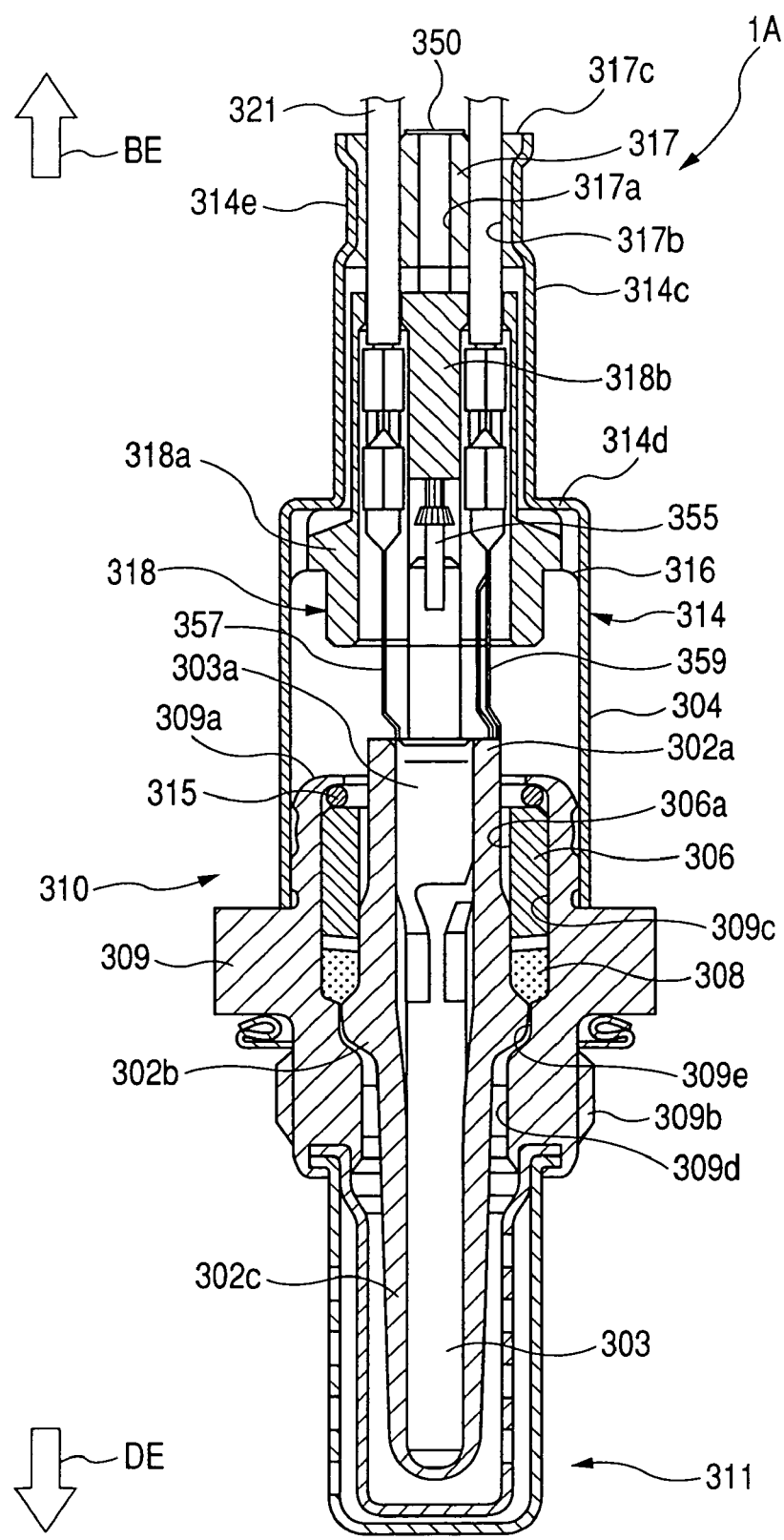
FIG. 3 is a longitudinal sectional view of a gas sensor of a second embodiment according to the present invention.

FIG. 3 is a longitudinal cross sectional view showing an overall structure of the gas sensor of the present embodiment.

As shown in FIG. 3, the gas sensor 1A comprises a tubular gas sensor element 302 with a distal end thereof being closed, and a columnar heater element 303 composed of a ceramic heater.

The gas sensor element 1A is made of a solid electrolyte body having oxygen ion conductivity.

As shown in FIG. 3, the gas sensor 1A further comprise a metallic housing body 309 having an end portion formed with a screw portion 309b, available to be screwed into a threaded portion of an exhaust pipe of an automotive engine for mounting the gas sensor thereon, and a base portion formed with an annular flange 309a extending radially inward from a distal end of the base end of the housing body 309.

The base portion of the housing body 309 is internally formed with a first central hole 309c and the end portion of the housing body 309 is internally formed with a second central hole 309d, with a third intermediate hole 309e being formed inside the housing body 309 between the first and second holes 309c and 309d. The first central hole 309c is larger in diameter than the intermediate hole 309e that is larger in diameter than that of the second central hole 309d.

The gas sensor element 302 has a base portion 302a axially extending through the first hole 309c formed on the base portion of the housing body 309 and protrudes from the annular flange 309a of the housing body 309 into an internal space defined inside the atmosphere-side cover 314, an intermediate cylindrical portion 302b having an end portion fitted to and supported with the intermediate hole 309e of the housing body 309, and an end portion 302c extending through the second central hole 309d of the housing body 309 and having a major portion thereof being accommodated inside the measuring gas-side cover 311.

A cylindrical insulator 306 is inserted through the first central hole 309c and has an inner wall 306a with which an end portion of the base portion 302a of the gas sensor element 302 is fixedly supported in electrical insulation with respect to the housing body 309.

Ceramic powder 308 is placed in an annular space between the first central bore 309c of the housing body 309 and an outer circumferential periphery of the base portion 302a.

Further, an annular ring 315 is sandwiched between an end face of the cylindrical insulator 306 and the annular flange 309a folded inward from the end of the base portion of the housing body 309, thereby holding the cylindrical insulator 306 and the ceramic powder 308 in fixed places.

The atmosphere-side cover 304 comprises a main cylindrical cover body 314a, having an end portion fitted to and fixedly secured to the base end of the housing body 309, and a secondary cylindrical cover body 314c axially extending upward from an annular shoulder 314d radially extending inward from a base end of the main cylindrical cover body 314a. The secondary cylindrical cover body 314c has a base portion formed with a caulked portion 314e with which a seal member 317, made of resilient material such as rubber, is fixedly supported in gastight sealing effect.

In addition, an insulator guide 318 is fixedly retained with the main cylindrical cover body 314 of the atmosphere-side cover 314 by means of a biasing spring 316 disposed between an insulator body 318a of the insulator guide 318 and the main cylindrical cover body 314 of the atmosphere-side cover 314.

The insulator guide 318 has a central portion 318b having a distal end mechanically connected to a base end of the heater element 303 via a support pin 355. The heater element 303 has a base portion formed with terminal electrodes 303a that are electrically connected to selected ones of the lead wires 321 through connecting members 357. Likewise, the gas sensor element 302 has the base portion formed with terminal electrodes (not shown) that are connected to remaining ones of the lead wires 321 through connecting members 359. The connecting members 357 and 359 extend through an annular bore 318c formed inside the insulator guide 318.

Further, the seal member 317 has a central area formed with an axially extending ventilation bore 317a around which a plurality of lead wire insertion bores 317b are formed for insertion of lead wires 321.

With the gas sensor 1A of the present embodiment, a ventilation filter 350 is fusion bonded to an end face 317c of the seal member 317 in a fusion-bonded area at temperatures above 300° C. The fusion-bonded area is formed in an entire circumference with no clearance being provided in the bonding area. Further, the ventilation filter 350 is located on the end face of the seal member 317. Furthermore, a surface area A of the ventilation bore 317a in a radial cross section of the end face portion of the seal member 317 lies in a value of 1 mm² and a surface area B of a region surrounded with the fusion-bonded area lies in a value of 9 mm², and the relationship is established as $A < B \leq 9A$ Thus, no annular edge portion of the ventilation filter 350 flops over the lead wire insertion bores 317b formed in the seal member 317. In addition, such a structure enables the ventilation bore 317a and the lead wire insertion bores 317b to be placed closer in distance to each other, thereby making it possible to minimize a whole of the seal member 317.

As set forth above, with the gas sensor 1A adopting such a structure, the gas sensor can be miniaturized in structure without causing the annular edge portion of the ventilation filter 350 from flopping over the lead wire insertion bores 317b formed in the seal member 317.

Third Embodiment

A gas sensor of a second embodiment according to the present invention is described below with reference to FIG. 4.

Figure 4:
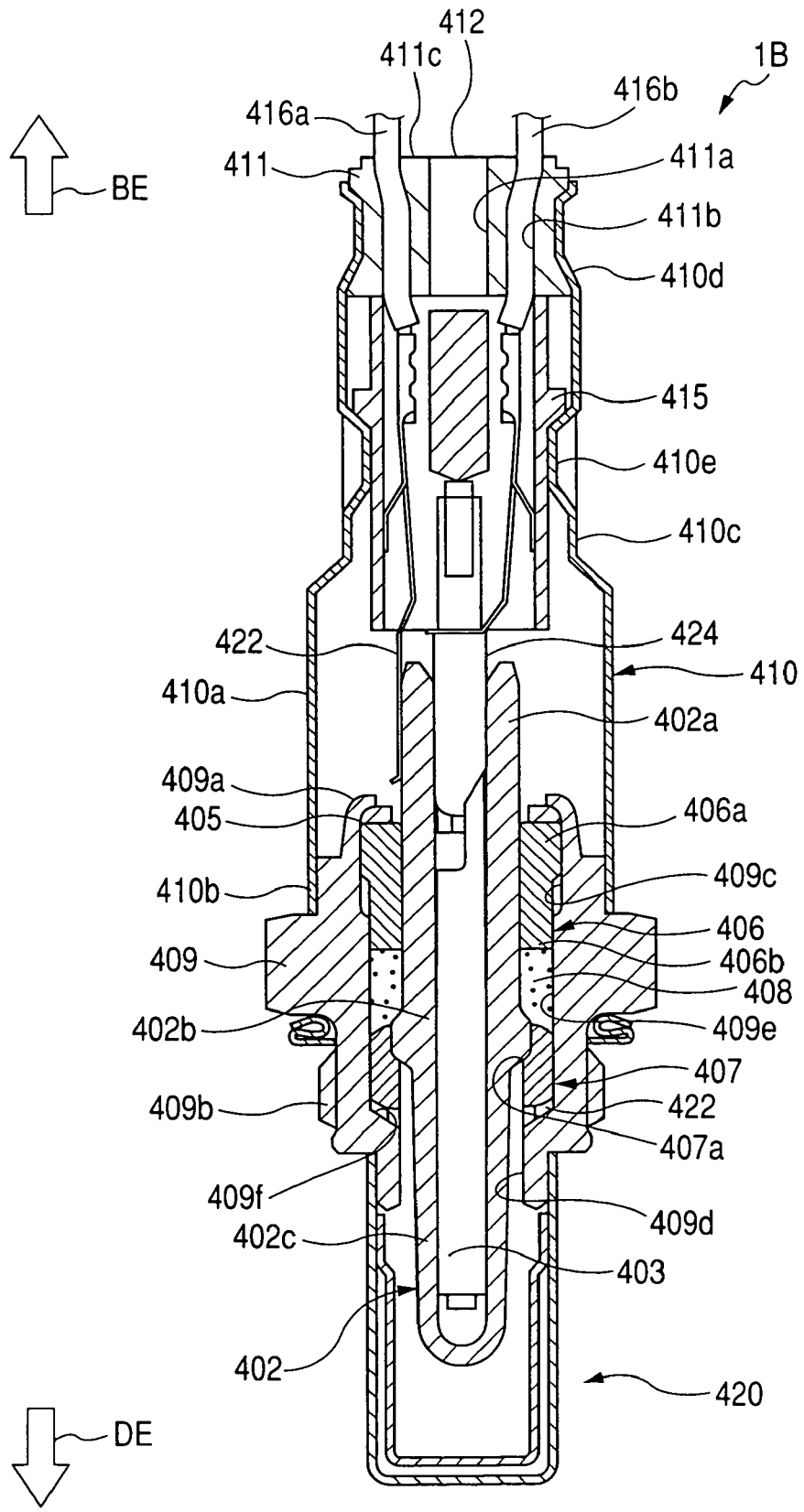
FIG. 4 is a longitudinal sectional view of a gas sensor of a third embodiment according to the present invention.

FIG. 4 is a longitudinal cross sectional view showing an overall structure of the gas sensor of the present embodiment.

As shown in FIG. 4, the gas sensor 1B comprises a tubular gas sensor element 402 with a distal end thereof being closed, a columnar heater element 403 composed of a ceramic heater, a metallic housing body 409, an atmosphere-side cover 410, and a measuring gas-side cover 420.

The housing body 409 has an end portion formed with a screw portion 409b, available to be screwed into a threaded portion of an exhaust pipe of an automotive engine for mounting the gas sensor thereon, and a base portion formed with an annular flange 409a extending radially inward from a distal end of the base end of the housing body 409.

The base portion of the housing body 409 is internally formed with a first central hole 409c and the end portion of the housing body 409 is internally formed with a second central hole 409d, with a third intermediate hole 409e being formed inside the housing body 409 between the first and second holes 409c and 409d. The first central hole 409c is larger in diameter than the intermediate hole 409e that is larger in diameter than that of the second central hole 409d.

The gas sensor element 402 has a base portion 402a axially extending through the first hole 409c formed on the base portion of the housing body 409 and protrudes from the annular flange 409a of the housing body 409 into an internal space defined inside the atmosphere-side cover 410, an intermediate cylindrical portion 402b having an end portion fitted to and supported with the intermediate hole 409e of the housing body 409, and an end portion 402c extending through the second central hole 409d of the housing body 409 and having a major portion thereof being accommodated inside the measuring gas-side cover 420.

The housing body 409 incorporates therein first and second tubular insulators 406 and 407 in an axially spaced relationship. In particular, the first tubular insulator 406 has a head portion 406 disposed in the first hole 409c of the housing body 409 and a cylindrical portion 406b disposed in the intermediate hole 409e of the housing body 409. The second tubular insulator 407, having an inner annular shoulder 407a, is disposed in the intermediate hole 409e and rests on a tapered annular shoulder 409f of the housing body 409 via a packing 422.

Ceramic powder 408 is placed in an annular space between the intermediate central bore 409e of the housing body 409 and an outer circumferential periphery of the base portion 402a of the gas sensor element 402 in an area between the first and second tubular insulators 406 and 407. With such a structure, the gas sensor element 40a is mounted on an exhaust pipe of an automotive engine with the closed end of the gas sensor element 402 protruding into the exhaust pipe.

With the gas sensor 1B mounted on the exhaust pipe of the automotive engine, further, the measuring gas-side cover 420 is fixedly secured to an end portion of the housing body 409 and exposed to high temperature gases passing through the exhaust pipe.

Further, an annular ring 405 is sandwiched between an end face of the first tubular insulator 406 and the annular flange 409a folded inward from the end of the base portion of the housing body 409, thereby holding the ceramic insulators 406, 407 and the ceramic powder 408 in fixed places.

The atmosphere-side cover 410 comprises a main cylindrical cover body 410a, having an end portion 410b fitted to and fixedly secured to the base end of the housing body 409, and a secondary cylindrical cover body 410c axially extending upward from the other end of the main cylindrical cover body 410a. The secondary cylindrical cover body 410c has first and second caulked portions 410d, 410e.

The first caulked portion 410d fixedly supports a columnar-shaped seal member 411, made of resilient material such as rubber, at an open end of the secondary cylindrical cover body 410c in gastight sealing effect. In addition, an insulator guide 415 is fixedly supported with the second caulked portion 410e in contact with a bottom wall of the seal member 411 and acts as a member to guide a connecting member 422, through which the gas sensor element 402 is electrically connected to the lead wires 416, and a connecting member 424 through which the ceramic heater 403 is electrically connected to lead wires 416b.

Further, the seal member 411 has a central area formed with an axially extending ventilation bore 411a around which a plurality of lead wire insertion bores 411b are formed for insertion of the lead wires 416a, 416b.

With the gas sensor 1B of the present embodiment, a ventilation filter 412 is fusion bonded to an end face 411c of the seal member 411 in a fusion-bonded area at temperatures above 300° C. The fusion-bonded area is formed in an entire circumference with no clearance being provided in the bonding area. Further, the ventilation filter 412 is located on the end face 411c of the seal member 411. Furthermore, a surface area A of the ventilation bore 411a in a radial cross section of the end face portion 411c of the seal member 411 lies in a value of 1 mm² and a surface area B of a region surrounded with the fusion-bonded area lies in a value of 9 mm², and the relationship is established as $$A < B \leq 9A$$

Thus, no annular edge portion of the ventilation filter 412 flops over the lead wire insertion bores 411b formed in the seal member 411. In addition, such a structure enables the ventilation bore 411a and the lead wire insertion bores 411b to be placed closer in distance to each other, thereby making it possible to minimize a whole of the seal member 411.

As set forth above, with the gas sensor 1B adopting such a structure, the gas sensor can be miniaturized in structure without causing the annular edge portion of the ventilation filter 412 from flopping over the lead wire insertion bores 411b formed in the seal member 411.

(Modified Form)

A gas sensor 1C of a modified form of the gas sensor of the first embodiment is described below with reference to FIGS. 5A and 5B.

Figure 5A:
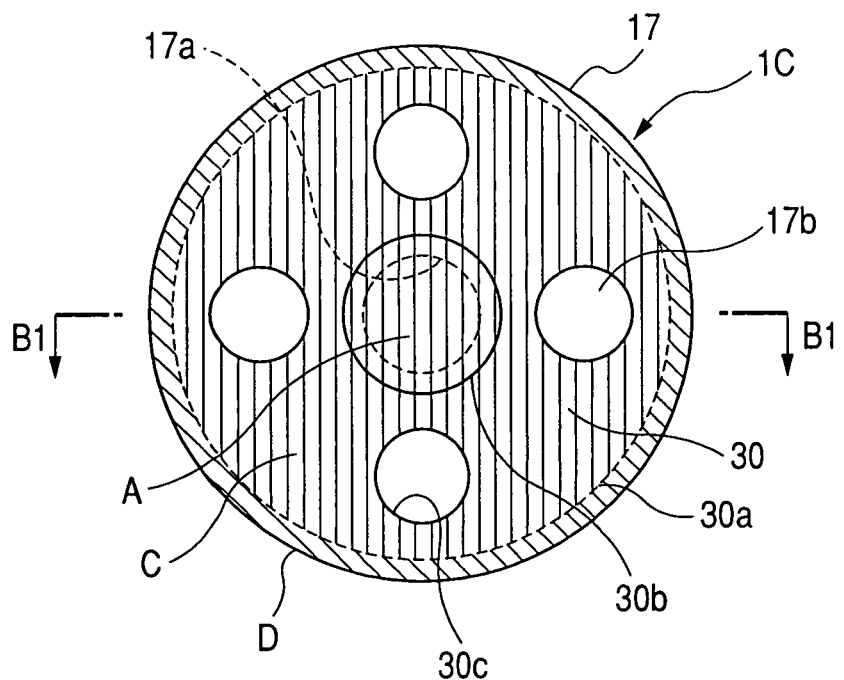
FIG. 5A is an enlarged view showing a seal member and a ventilation filter forming parts of a gas sensor of a modified form.
Figure 5B:
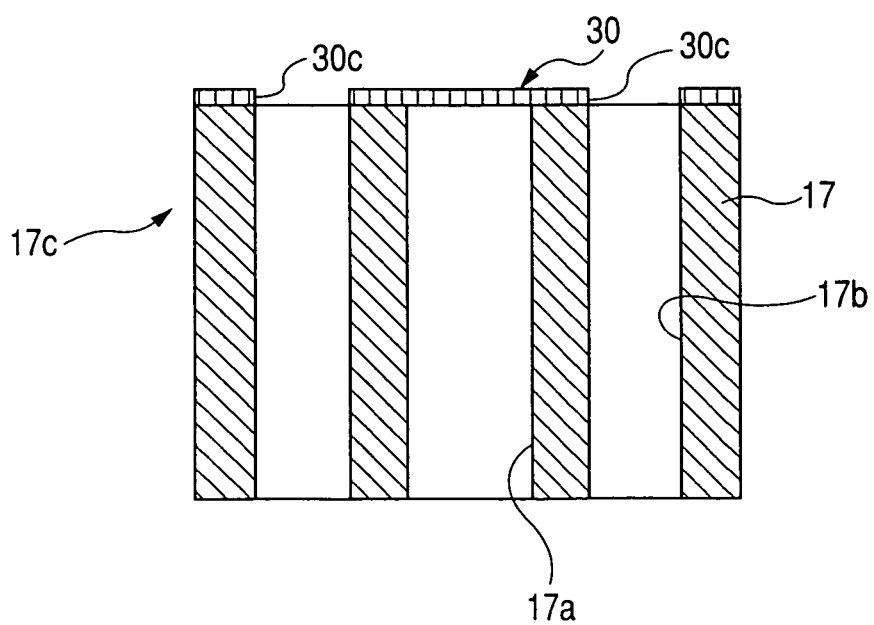
FIG. 5B is a cross sectional view taken on line B1-B1 of FIG. 5A.

FIGS. 5A and 5B are enlarged views showing a seal member and a ventilation filter forming parts of the gas sensor of the present modification. FIG. 5A is a view of the seal member and the ventilation filter as viewed from a base-end (from an upper area) of the gas sensor. FIG. 5B is a cross sectional view taken on line B1-B1 of FIG. 5A.

A ventilation filter 30, shown in FIGS. 5A and 5B, can be applied to the structure of the gas sensor 1 of the first embodiment shown in FIG. 1. That is, as shown in FIG. 1, the gas sensor 1 of the first embodiment comprises the gas sensor element 19 operative to detect a specified gas concentration of measuring gases, the cylindrical housing 10 through which the gas sensor element 19 extends and is fixed supported, the cylindrical measuring gas-side cover 11 fixedly secured to the distal end of the housing 10 so as to cover the distal end of the gas sensor element 19, and the cylindrical atmosphere-side cover 2 fixedly secured to the housing 10 at the base end thereof so as to cover the base end of the gas sensor element.

Further, the atmosphere-side cover 2 has the base end into which the seal member 17 is accommodated in a fixed place. The seal member 17 has the central area formed with the axially extending ventilation bore 17a for introducing atmospheric air to the inside of the atmosphere-side cover 2. The seal member 17 also has a plurality of axially extending lead wire insertion bores 17b formed at circumferentially spaced positions in the area around the ventilation bore 17a.

With the gas sensor of the present modification, the ventilation filter 30 is fusion bonded to the base end portion 17c of the seal member 17 in a fusion-bonded area 30b at temperatures above 300° C. (that is, at temperatures above melting point of the filter). The fusion-bonded area 30b can be formed upon causing an annular heating member with a diameter smaller than that of the ventilation filter 30 to rise at a temperature higher than 300° C. and pressing the annular heating member against the seal member 17 via the ventilation filter 30.

Further, the fusion-bonded area 30b, made of the seal member 17 and the ventilation filter 30 which are fusion-bonded to each other, is formed in an entire circumference with no clearance being formed at the fusion bonded portion. With such an arrangement, no clearance is formed between the seal member 17 and the ventilation filter 30, thereby preventing foreign substances from penetrating into the gas sensor 1 from an outside.

Further, locating the ventilation filter 30 at the base end portion 17c of the seal member 17 enables the ventilation filter 30 to be positioned remote from a distal end of the gas sensor 1. Such a placement provides capability of preventing pores of the ventilation filter 30, made of porous material, from being melted in deformation and stopped up due to heat with the resultant deterioration in air permeability.

Furthermore, the ventilation filter 30 has areas, corresponding to the lead wire insertion bores 17b of the seal member 17, which are formed with opening portions 30c and no ventilation filter 30 straddles over the lead wire insertion bores 17b of the seal member 17.

Moreover, suppose a surface area "A" of the ventilation bore 17a of the base end portion 17c of the seal member 17 in a radial direction is 3 mm$^2$ and a surface area "D" of the base end portion 17c of the seal member 17 is 314 mm$^2$ and a surface area "C" of the ventilation filter 30 is 264 mm$^2$, the relationship is established as $$A < C \leq D$$

Thus, the ventilation filter 30 can be fusion bonded to the seal member 17 in an increased fusion bonded area, providing an increased bonding reliability between the seal member 17 and the ventilation 30.

With the gas sensor of the present modification, as set forth above, a gas sensor can be provided which has no probability for the ventilation filter 30 to cover the lead wire insertion bores 17b formed in the seal member 17.

While the specific embodiments of the present invention have been described in detail, it will be appreciated by those skilled in the art that various modifications and alternatives to those details could be developed in light of the overall teachings of the disclosure. For instance, the material of the seal member includes not only fluorocarbon rubber but also other material, having heat resistance, such as silicone rubber or the like. Moreover, measuring gas may include not only oxygen gas but also other gas components such as NOx, CO, HC or the like. The gas sensor element may include any of structures including a stack type and a cup type.

What is claimed is:

1. A gas sensor comprising:
a gas sensor element for detecting a concentration of specified gas in measuring gases;
a cylindrical housing through which the sensor element extends and is fixedly supported;
an atmosphere-side cover fixedly secured to a base end of the cylindrical housing so as to cover a base end portion of the gas sensor element;
a seal member fixedly supported with a base end of the atmosphere-side cover and having a ventilation bore, through which atmospheric air is introduced to the cylindrical housing, and a plurality of lead wire inserting bores formed around the ventilation bore; and
a filter member, made of porous material and covering the ventilation bore so as to permeate atmospheric air, which has a fusion-bonded area in which the filter member is fusion bonded to an end face of the seal member at temperatures above 300° C.;
wherein the fusion-bonded area is formed in an entire circumference in gastight effect at an area outside an outer periphery of the ventilation bore covered with the filter member and has no clearance;
wherein suppose that the ventilation bore has an opening surface area A at the end face of the seal member and a region surrounded with the fusion-bonded area has a surface area B, the relationship is established as $$A < B \leq 9A.$$

2. The gas sensor according to claim 1, wherein:
the ventilation bore is formed in the seal member so as to extend in an axial direction; and
the filter member covers an end of the ventilation bore at the end face of the seal member.

3. The gas sensor according to claim 1, wherein:
the atmosphere-side cover comprises a main cylindrical cover body having one end connected to the cylindrical housing, an annular shoulder extending radially inward from the other end of the main cylindrical cover body, and a secondary cylindrical cover body axially extending from the annular shoulder of the main cylindrical cover body and having the base end with which the seal member is fixedly supported;
and further comprising:
an element-side insulator accommodated in the cylindrical housing and fixedly supporting the gas sensor element; and
an atmosphere-side insulator disposed between the element-side insulator and the annular shoulder of the main cylindrical housing.

4. The gas sensor according to claim 3, further comprising:
a packing member disposed between the element-side insulator and the cylindrical housing to provide a gastight sealing effect therebetween; and
a spring member disposed between the atmosphere-side insulator and the annular shoulder of the main cylindrical housing to press the element-side insulator and the atmosphere-side insulator against the packing member.

5. The gas sensor according to claim 1, wherein:
the atmosphere-side cover comprises a main cylindrical cover body having one end connected to the cylindrical housing, an annular shoulder extending radially inward from the other end of the main cylindrical cover body, and a secondary cylindrical cover body axially extending from the annular shoulder of the main cylindrical cover body and having the base end with which the seal member is fixedly supported; and the cylindrical housing has a base end portion formed with an inner bore and having a distal end formed with an annular flange extending radially inward;

and further comprising:

a cylindrical insulator accommodated in the inner bore of the cylindrical housing; and an annular spring member disposed between the annular flange of the cylindrical housing and one end of the cylindrical insulator.

6. The gas sensor according to claim 5, further comprising:

a heater element disposed inside the gas sensor element; and an insulator guide fixedly supported with the atmosphere-side cover for accommodating connecting members through which electrode terminals of the gas sensor element and electrode terminals of the heater element are connected to lead wires, respectively.

7. The gas sensor according to claim 1, wherein:

the atmosphere-side cover comprises a main cylindrical cover body having one end connected to the cylindrical housing, an annular shoulder extending radially inward from the other end of the main cylindrical cover body, and a secondary cylindrical cover body axially extending from the other end of the main cylindrical cover body and having a first portion, with which the seal member is fixedly supported, and a second portion axially spaced from the first portion in a position close to the main cylindrical cover body; and the cylindrical housing has a base end portion formed with an inner bore and having a distal end formed with an annular flange extending radially inward;

and further comprising:

a cylindrical insulator accommodated in the inner bore of the cylindrical housing; and an annular spring member disposed between the annular flange of the cylindrical housing and one end of the cylindrical insulator.

8. The gas sensor according to claim 7, further comprising:

a heater element disposed inside the gas sensor element; and an insulator guide fixedly supported with the second portion of the secondary cylindrical cover body for accommodating connecting members through which electrode terminals of the gas sensor element and electrode terminals of the heater element are connected to lead wires, respectively.

9. The gas sensor according to claim 1, wherein:

the filer member has an outer circumferential periphery located inside the plurality of lead wire insertion bores formed in the seal member.

10. The gas sensor according to claim 1, wherein:

the filer member has an outer circumferential periphery, extending in an area outside the plurality of lead wire insertion of the seal member, and has a plurality of bores formed at the same positions at which the plurality of lead wire insertion bores are formed in the seal member.

* * * * *